(12) United States Patent
Fugger

(10) Patent No.: US 10,561,481 B2
(45) Date of Patent: Feb. 18, 2020

(54) BATTERY CHASSIS WITH STROKE LIMITER DESIGN

(71) Applicant: KONINKLIJKE PHILIPS N.V., Eindhoven (NL)

(72) Inventor: Hannes Fugger, Rosenbach (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 263 days.

(21) Appl. No.: 15/576,885

(22) PCT Filed: May 12, 2016

(86) PCT No.: PCT/IB2016/052714
§ 371 (c)(1),
(2) Date: Nov. 27, 2017

(87) PCT Pub. No.: WO2016/189407
PCT Pub. Date: Dec. 1, 2016

(65) Prior Publication Data
US 2018/0147038 A1    May 31, 2018

Related U.S. Application Data

(60) Provisional application No. 62/166,736, filed on May 27, 2015.

(51) Int. Cl.
| | | |
|---|---|---|
| *A61C 17/34* | (2006.01) |
| *A61C 17/22* | (2006.01) |
| *H01M 2/10* | (2006.01) |
| *H02K 7/14* | (2006.01) |
| *H02K 33/00* | (2006.01) |

(52) U.S. Cl.
CPC .......... *A61C 17/34* (2013.01); *A61C 17/225* (2013.01); *H01M 2/1022* (2013.01); *H02K 7/14* (2013.01); *H02K 33/00* (2013.01); *H01M 2220/30* (2013.01)

(58) Field of Classification Search
CPC ..... A61C 17/225; A61C 17/224; A61C 17/34; A46B 13/02; H02K 5/24; H02K 7/145; H02K 7/14; H02K 33/00; H01M 2/1022
See application file for complete search history.

(56) References Cited

U.S. PATENT DOCUMENTS

| | | | |
|---|---|---|---|
| 2014/0259469 A1 | 9/2014 | Garrigues et al. | |
| 2016/0166367 A1* | 6/2016 | Kleppen | H02K 7/145 |
| | | | 310/38 |

FOREIGN PATENT DOCUMENTS

| | | | |
|---|---|---|---|
| JP | 2003189937 A | 7/2003 |
| WO | 2006115757 A1 | 11/2006 |
| WO | 2014033685 A2 | 3/2014 |

* cited by examiner

*Primary Examiner* — Shay Karls

(57) ABSTRACT

A battery chassis with stroke limiter (70) for a power toothbrush (10) configured to improve the durability of a power toothbrush (10) and to simplify the assembly process. The battery chassis stroke limiter (70) provides a secure housing for the battery (80), while tolerance compensation leaves (71, 72), and battery hardstops (75, 76, 77) provide for drop mitigation protection and shock protection, as well as vibration mitigation.

15 Claims, 8 Drawing Sheets

BATTERY CHASSIS WITH STROKE LIMITER DESIGN

CROSS-REFERENCE TO PRIOR APPLICATIONS

This application is the U.S. National Phase application under 35 U.S.C. § 371 of International Application No. PCT/IB 2016/052714, filed on May 12, 2016, which claims the benefit of U.S. Provisional Patent Application No. 62/166,736, filed on May 27, 2015. These applications are hereby incorporated by reference herein.

Aspects of this invention relate generally to motor-driven powered toothbrushes. More particularly, the invention relates to toothbrush features which promote greater durability and control of vibrations transmitted to the user through the toothbrush handle while facilitating ease of manufacturing assembly.

Power toothbrushes are in general well known and encompass a wide variety of designs and physical arrangements. Many power toothbrushes have a rotary-type motion. Some have the capability of a 360° armature rotation, but due to design arrangements produce an oscillatory movement limited to a particular range of motion, i.e. a selected arcuate portion of 360°, in order to provide a more suitable brushing effect. Some of these rotary motion devices are mechanically driven, while others are resonant systems, involving a movable mass such as a brushhead structure and a spring which is attached to the handle. Various designs provide an optimized interaction of brushhead frequencies and motion amplitude, where amplitude is further driven by the size of the brushhead and the amplitude of shaft rotation.

Several problems arise in reciprocating or sweeping motion power toothbrushes. First, plastic injection-molded parts are commonly used in the housing and component parts. These component parts are necessary to hold the internal functional parts together (i.e. battery, motor, printed circuit board assembly, etc.) The parts must be rugged enough to withstand the motor motion, while providing support for the various parts, as well as providing protection for the parts. However, a larger number of component parts adds to manufacturing costs and time. There is a need to reduce cost by creating modular parts that mate with each other, each part having several complex functions. Especially desired is a system of low-cost parts which improve the durability of the device by absorbing axial and lateral shocks. Axial shocks can, for example, be experienced if the toothbrush is dropped. Dropping can cause failure of components such as the battery or printed circuit board, and could also cause damage to the plastic parts. A secondary desired result for these features is lower material and assembly costs and simplified assembly methods and reduced assembly time.

Yet another problem which arises is that existing frame designs are too expensive. There is a need to reduce cost by creating modular parts that mate with the frame, each part having several complex functions. Especially desired is a system of low-cost parts which improve the durability of the device by absorbing axial shocks. Axial shocks can, for example, be experienced if the toothbrush is dropped on the end of its shaft. A secondary desired result for these features is lower material and assembly costs.

The present invention provides a solution to the deficiencies in the prior art through use of components that serve multiple functions in holding, securing and protecting parts, while simplifying assembly methods and insertion of parts into a single-part frame assembly. Additionally, the motor is the main vibration creation mechanism in the system, the invention innovatively addresses the problem of vibration isolation. In particular, the present invention relies upon the use of an elastomeric material to form the multi-function components, and then attaching those elastomeric components to a plastic injection-molded frame. The majority of the vibration energy is directed into the elastomeric material where it dissipates before reaching the housing where it can be transferred to the user. Additionally, these elastomeric material components also hold the one or more rechargeable batteries, which are of a substantial weight comparatively with the rest of the components. In earlier models of such devices, if the device is dropped, the weight of the battery can cause damage to other mechanical or electrical components, or the holding structure and frame, or even to the batteries themselves. By isolating the batteries within various elastomeric components that have features to absorb the axial shock and motion, the damage can be minimized or eliminated, thus causing less product failures.

In one embodiment of the invention, a battery chassis/stroke limiter for a power toothbrush is disclosed. The battery chassis/stroke limiter has a substantially hollow portion for holding a portion of a rechargeable battery that powers the power toothbrush. The battery chassis/stroke limiter also has tolerance compensation leaves disposed in a compressive arrangement between a distal end of the battery and the distal portion of the battery chassis/stroke limiter, and first, second and third battery hardstops for limiting axial motion of the battery. The battery chassis/stroke limiter has guiding ribs for compressibly holding the battery chassis/stroke limiter in grooves in the interior of the housing of the power toothbrush.

In another embodiment, a system for mitigating mechanical shock in a power toothbrush is disclosed. The power toothbrush has an elongated housing open at a distal end and a proximal end, and a unitary subassembly configured to be disposed in the housing. The unitary subassembly has a battery, a control circuit in electrical communication with the battery, a drive mechanism having a drive shaft at a distal end thereof, the drive shaft configured to project through the opening at the distal end of the housing, the drive shaft arranged to receive a toothbrush brushhead. The unitary subassembly further comprises a battery chassis/stroke limiter for holding at least a portion of the battery, the battery chassis/stroke limiter including tolerance compensation leaves and first, second and third battery hardstops for absorbing vibration from the unitary subassembly and stopping excessive motion of the battery in the event of dropping of the power toothbrush. The unitary subassembly further includes a housing interlock for holding at least a portion of the battery, the housing interlock disposed in resilient contact with grooves in the interior wall of the proximal end of the housing, the housing interlock configured to hold together in compressive pressure the components of the unitary subassembly. The system further includes an end cap inserted into the opening at the proximal end of the housing to secure the unitary subassembly into the housing in the correct orientation and with proper pressure to maintain interaction of the components during normal operation and protect against damage in the event of sudden motion of the toothbrush, such as if it is dropped.

IN THE DRAWINGS

Figure 5A:
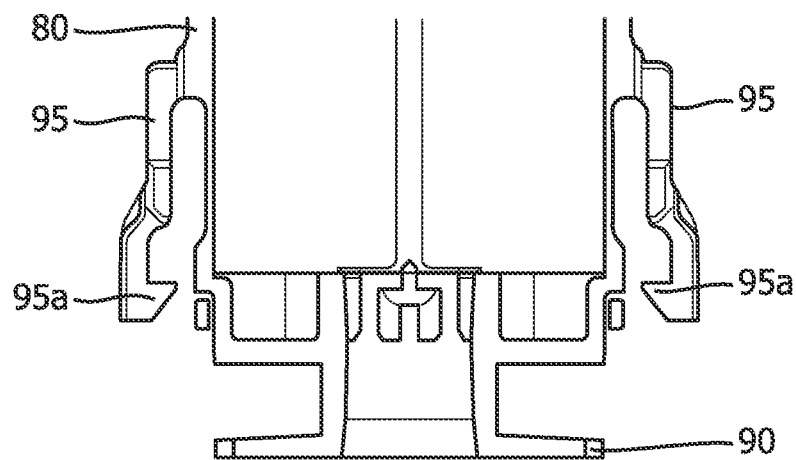
Figure 5B:
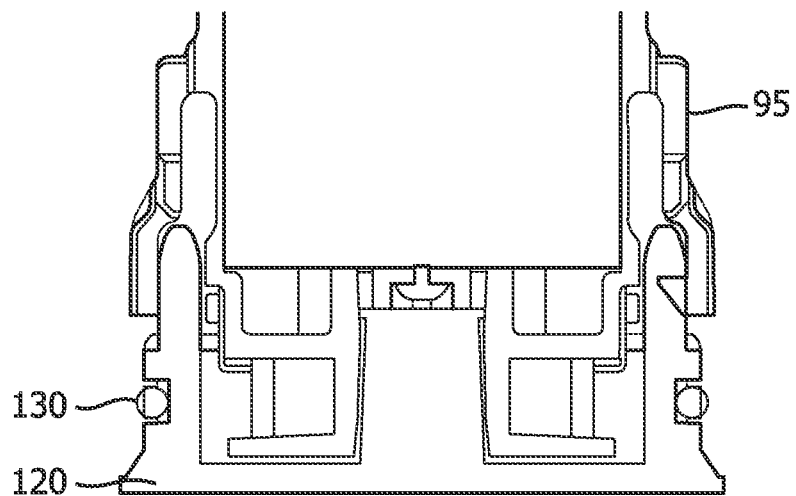
Figure 5C:
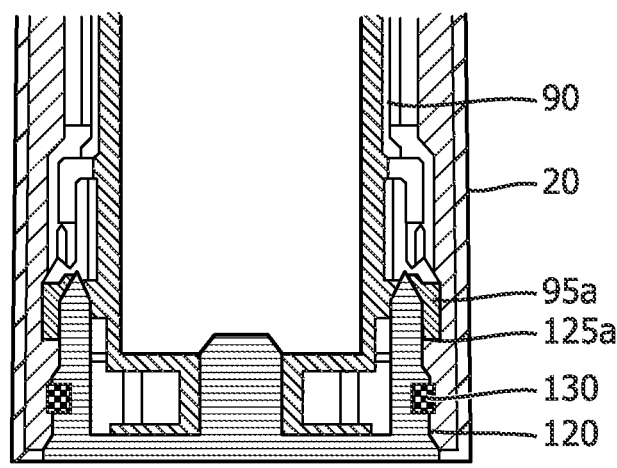
Figure 6:
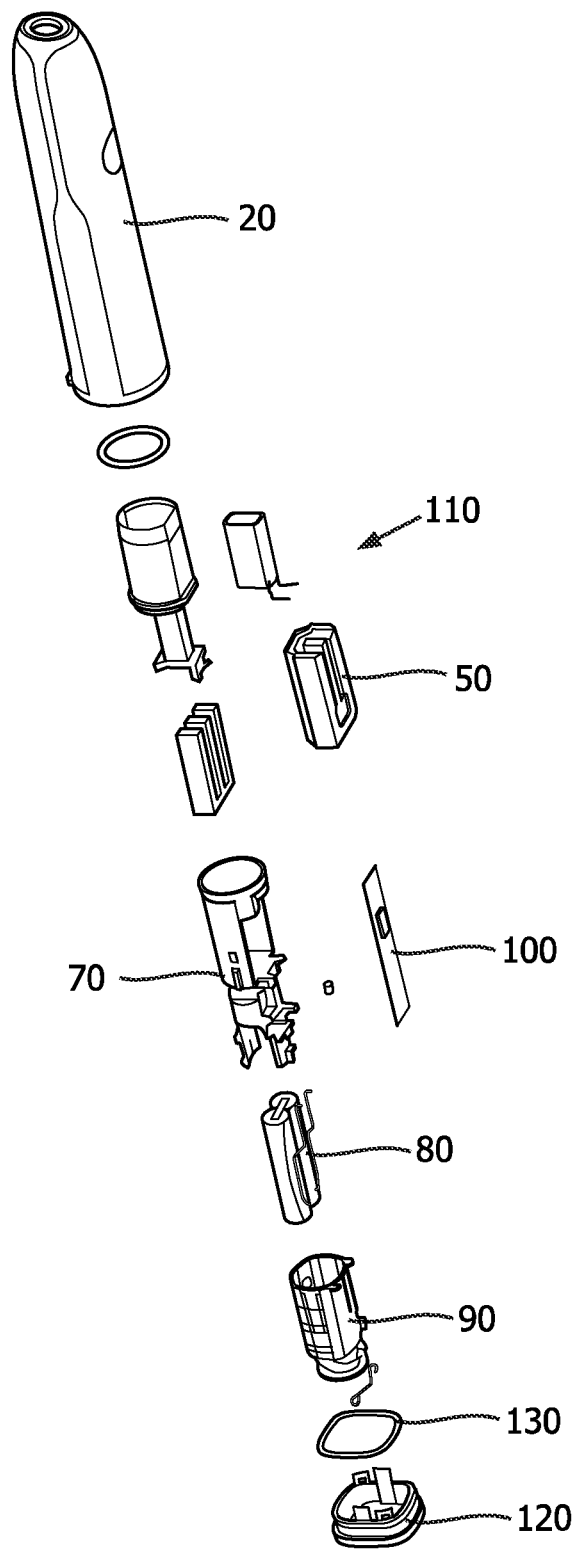
Figure 7:
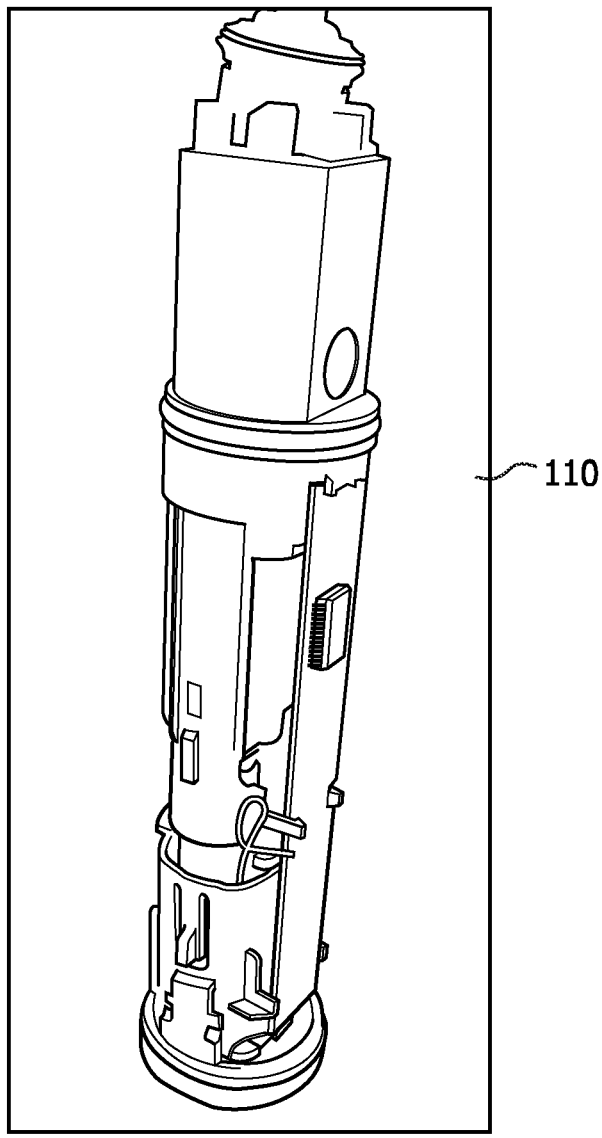
Figure 8:
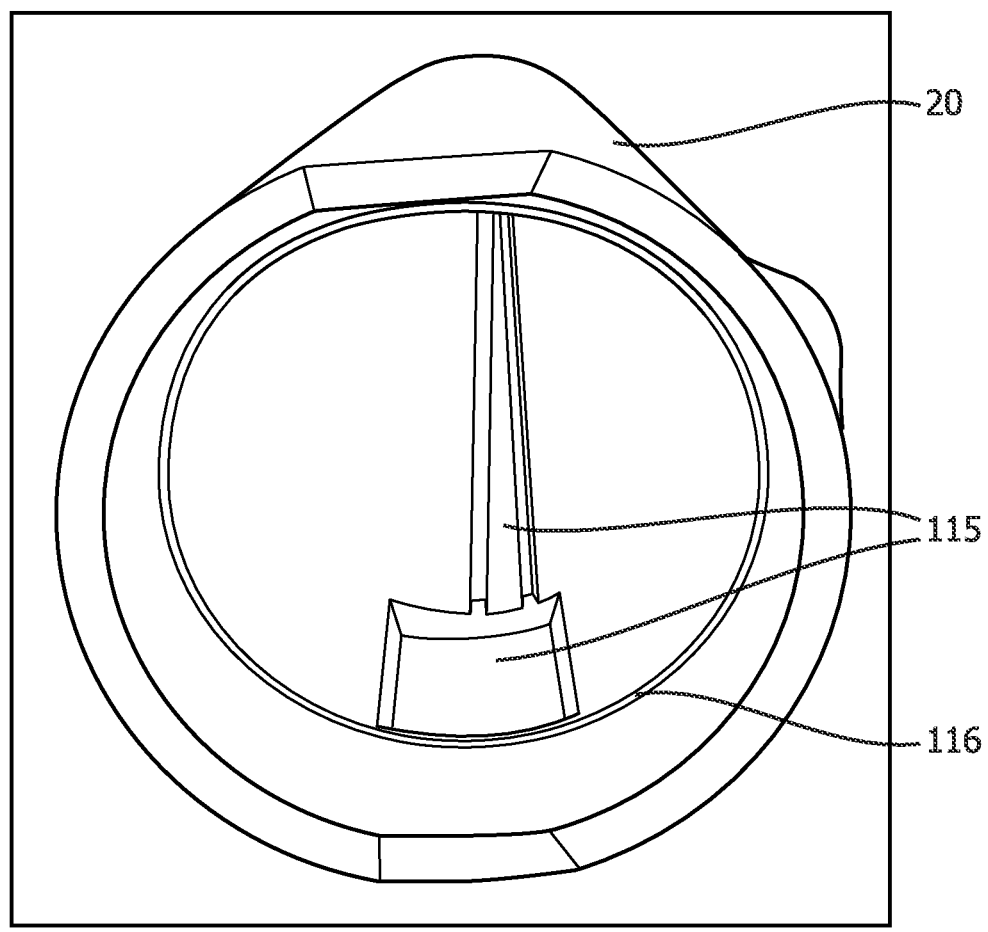

FIGS. 5A 5B and 5C are cutaway views of the housing interlock and end cap of the present invention;

FIG. 6 is an exploded assembly view of the components of a power toothbrush of the present invention;

FIG. 7 is an assembled view of the components of a power toothbrush of the present invention; and FIG. 8 is an interior view of a housing of the present invention viewed through the open proximal end of the housing.

Figure 1:
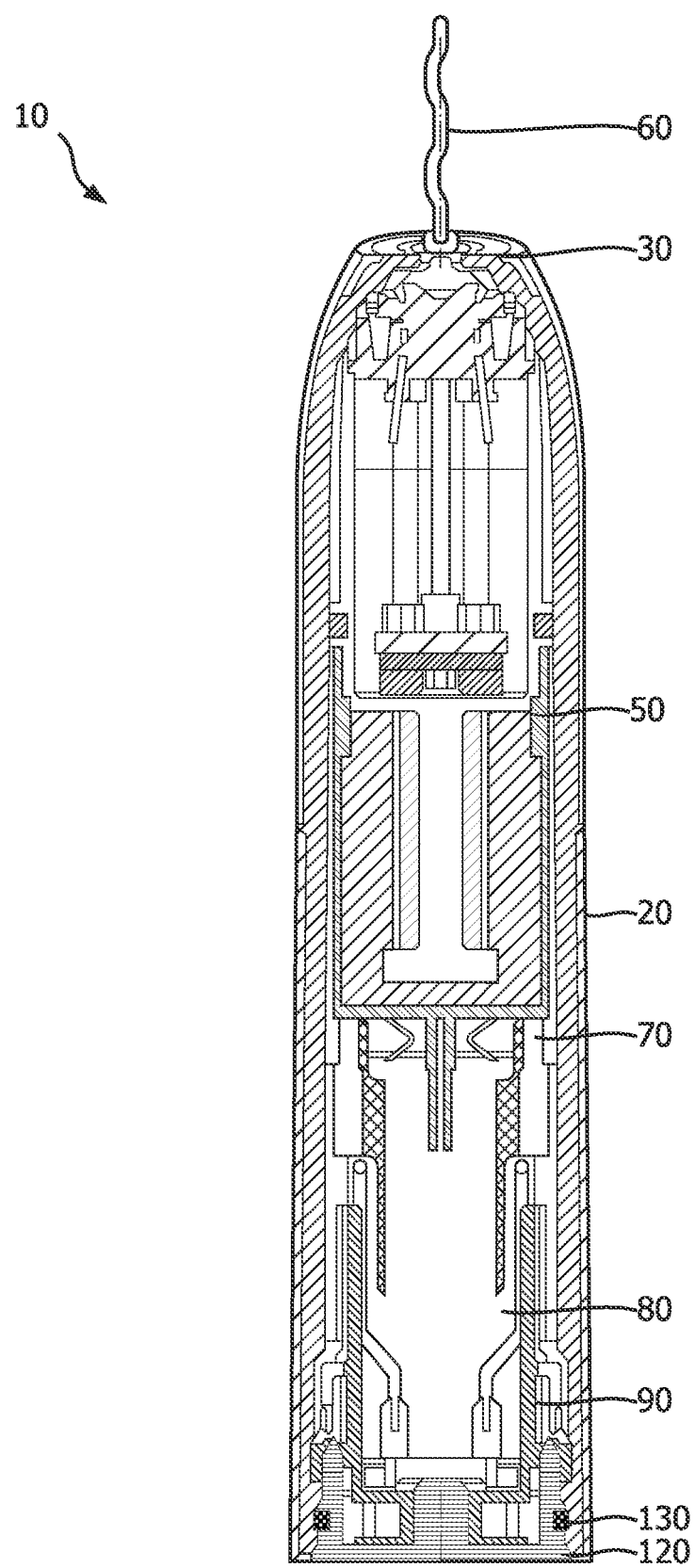
FIG. 1 illustrates a cut-away longitudinal view of a toothbrush assembly of the present invention.

FIG. 1 illustrates an assembly for a power toothbrush 10 of the present invention. Most components of the power toothbrush 10 are contained within an elongated housing 20 that is preferably sized to fit comfortably in a human hand. Preferably of a rigid and lightweight plastic, the housing 20 protects and seals internal components from shock and water ingress. Housing 20 includes an opening at the distal end, from which a distal end of drive shaft 60 protrudes, through a gasket 30 that protects against fluid egress into the housing 20. A toothbrush brushhead can be affixed to the distal end of the drive shaft. Housing 20 also has an opening at a proximal end, which is configured to receive an end cap 120. A gasket 130 within a groove on end cap 120 protects against fluid egress into the housing 20. Nested within the housing is a drive mechanism 50. The proximal end of drive shaft 60 is connected to the drive mechanism for providing movement to the drive shaft. One or more rechargeable batteries 80 is also disposed in the housing, contained within the battery chassis/stroke limiter 70 and the housing interlock 90. A control circuit board 100 is also contained within the housing 20, as shown in FIGS. 6 and 7.

Arranged distal to and encompassing a portion of battery 80 is a battery chassis/stroke limiter 70. It is designed to hold the battery 80 within frame 20. As will be described in more detail below, relating to FIGS. 2A through 2C, battery chassis/stroke limiter 70 is particularly characterized by having features which are arranged to limit the stroke, or movement of the battery, that can occur when the power toothbrush is dropped or shaken, and to absorb vibration from the battery 80 and drive mechanism 50 during normal operation. Battery chassis/stroke limiter 70 is also disposed to be in a compressive arrangement between the drive mechanism 50/battery 80 and other components of the power toothbrush 10, and a side surface of the housing 20.

As can be seen in FIG. 1, arranged proximal to and encompassing a portion of battery 80 is a housing interlock 90. Housing interlock 90 is constructed to hold the battery 80 and other components within housing 20 in a compressive arrangement with the inside of housing 20, and in a pressure fit with the housing and other components in conjunction with the end cap 120. The housing interlock 90 also has features shown in FIGS. 3A-3B, described following, which cushions against axial shock and provides tolerance mitigation during assembly. Also as shown in more detail in FIGS. 5A -5C, housing interlock 90 and end cap 120 are further engaged to the inside wall of the housing 20 proximal end by means of tabs and slots or equivalent, such that the housing interlock 90 compressibly biases against the housing 20 distal end to further secure components within the housing 20 and against housing distal end.

Figure 2A:
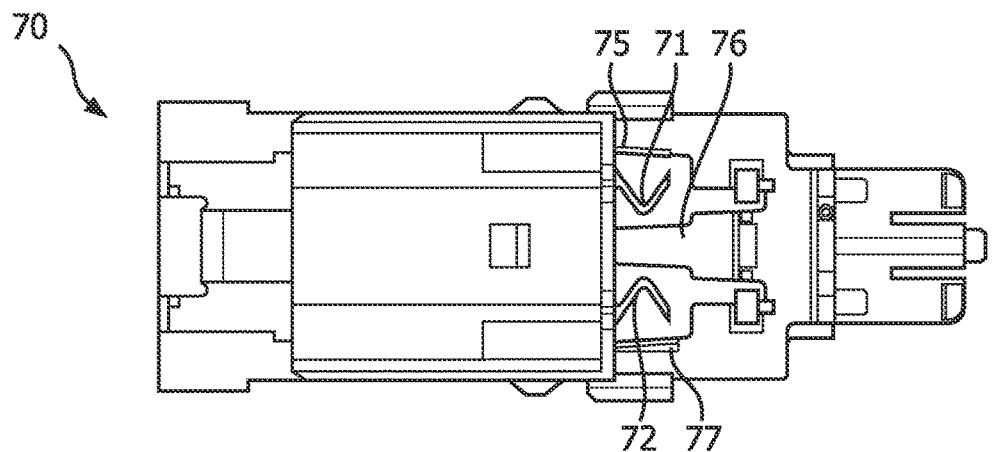
FIGS. 2A-2C illustrate a battery chassis stroke limiter for a power toothbrush, according to another embodiment of the invention.
Figure 2B:
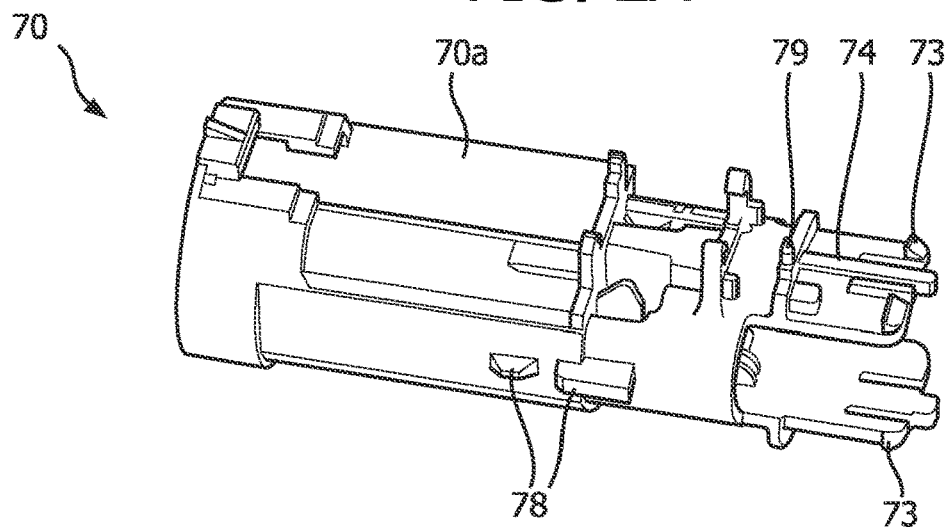
Figure 2C:
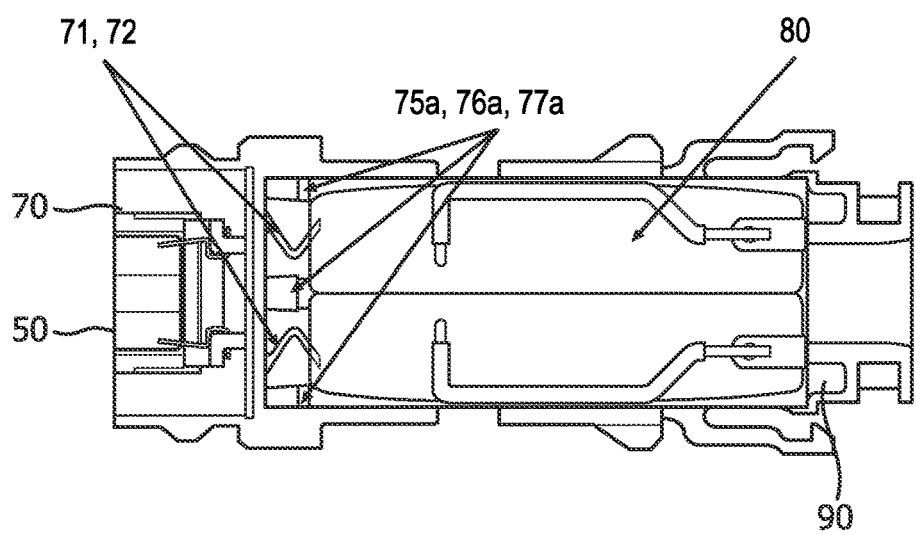

Now turning to FIGS. 2A, 2B, and 2C, there are illustrated particular embodiments of the battery chassis/stroke limiter 70 of the present invention, which is particularly characterized by having features which are arranged to limit the stroke, or movement of the battery 80. The battery 80 is a significant portion of the weight of the power toothbrush 10, and requires additional support and cushioning to protect against component damage if the power toothbrush 10 is dropped. Battery chassis/stroke limiter 70 is also disposed to be in a compressive arrangement between the battery 80 and a side surface of the housing 20 by means of guiding ribs (78) for support and cushioning and to absorb vibration caused by the drive mechanism 50 and/or battery 80 during normal operation so that vibration is not transmitted to the hand of the user, or the amount transmitted in reduced or minimized.

The embodiment shown in FIGS. 2A and 2B is a battery chassis/stroke limiter 70 having tolerance compensation leaves 71, 72 and first, second and third battery hard stops 75, 76, 77. Tolerance compensation leaves 71, 72 are disposed in a compressive arrangement between battery 80, and the distal portion of the battery chassis 70 that contains the battery 80, which is also the proximal end of portion of the battery chassis 70 that contains the drive mechanism 50. Tolerance compensation leaves 71, 72 function to limit and slow the axial displacement of the battery 80, and to absorb energy from the battery if it strikes the tolerance compensation leaves, 71, 72, and/or the battery hard stops 75, 76, 77 as shown in FIG. 2C, so as to reduce the energy of impact if the battery 80 should contact the battery hard stops 75, 76, 77. Similarly, horizontal stops 79 on the front and rear of the battery chassis/stroke limiter 70, as shown in FIG. 2B, are designed to serve a purpose similar to that of the battery hard stops 75, 76, 77. When battery chassis/stroke limiter 70 and interlock housing 90 are assembled together with battery 80 contained therein, horizontal stops 79 are positioned just above the distal end of interlock housing 90. Horizontal stops 79 will limit excessive distal direction movement of the housing interlock 90 and the battery 80 contained therein and stop displacement to prevent damage to components.

Battery hard stops 75, 76, 77 are disposed between the battery 80 and the distal portion of the battery chassis/stroke limiter 70 that contains the battery 80. As seen in FIG. 2C, each of the battery hard stops 75, 76, 77 includes at least one compression surface 75a, 76a, 77a, disposed at the proximal end of the hard stop, closest to the battery, which is shaped to contact a portion of the battery 80 distal end in the event of excessive battery motion in the axial plane. In normal operation of the power toothbrush 10, the tolerance compensation leaves 71, 72 are in contact with the distal end of the battery 80, to absorb the small amounts of motion and vibration that occur during use and reduce transfer of that motion and vibration to the user's hand, to provide a better operating experience. If the power toothbrush 10 is dropped or otherwise experiences excessive axial direction motion, the tolerance compensation leaves 71, 72 also serve to absorb the axial direction motion of the battery, and help to slow the sudden acceleration of the battery. The tolerance compensation leaves 71, 72 may absorb sufficient energy to arrest the motion of the battery 80 before it contacts the compression surface 75a, 76a, 77a of the battery hard stops 75, 76, 77, or may absorb sufficient energy to slow the contact of the battery with the hard stop compression surfaces, thereby minimizing impact and potential component failure, including damage to the tolerance compensation leaves 71, 72, drive mechanism 50, battery 80, and control circuit board 100. The battery chassis/stroke limiter 70 also serves to prevent excessive rotation of the shaft 60 during incidents of excessive force.

Figure 3A:
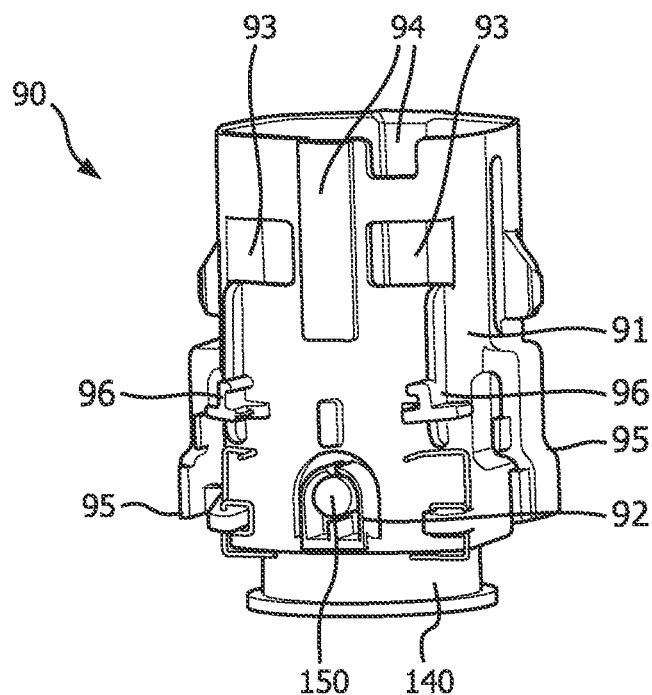
FIG. 3A-3B illustrate a housing interlock for a power toothbrush, according to another embodiment of the invention.
Figure 3B:
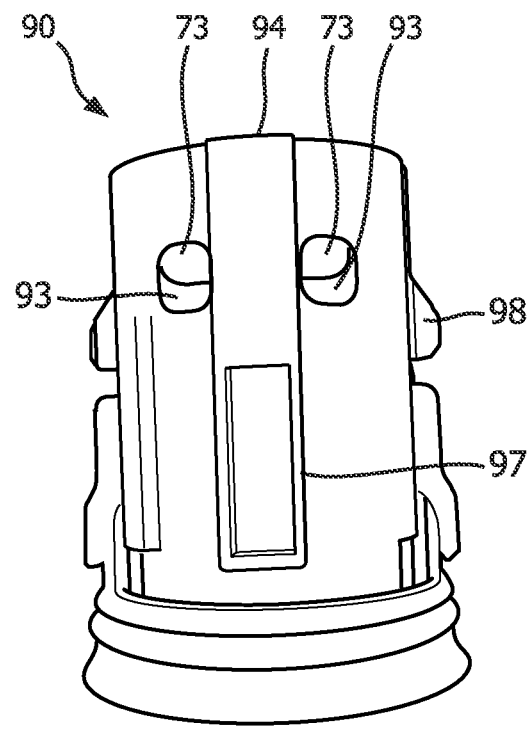

The battery chassis tabs 73 on the battery chassis/stroke limiter 70 are designed to interface with slots 93 on the interlock housing 90, shown in FIGS. 3A and 3B During manufacture, when the interlock housing 90 is attached to the battery chassis/stroke limiter 70, the tabs 73 snap into the slots 93, and help properly position and align the two components 70, 90 with respect to each other, as well as the battery 80 held within the two components. The ribs 74 on the front and rear of the battery chassis/stroke limiter 70 are designed to interface with the grooves 94 on the interlock housing 90, shown in FIG. 3A. During manufacture, when the interlock housing 90 is attached to the battery chassis/stroke limiter 70, the ribs 74 slide into the grooves 94, and help properly position and align the two components 70, 90, with respect to each other, as well as the battery 80 held within the two components.

At least one guiding rib 78 on each side of the battery chassis/stroke limiter 70 may engage in corresponding grooves 115 (shown in FIG. 8) that run along both sides of the inside of housing 20 to prevent battery chassis/stroke limiter 70 and battery 80 from rotating within the housing 20. The guiding ribs 78 also serve to protect components during sudden axial motion by absorbing force as well as limiting rotation. Further, the guiding ribs 78 serve to simplify factory manufacturing process, as described in more detail in association with FIGS. 6 and 7, below. Because the assembled components are held together by means of the battery chassis 70 and housing interlock 90 and their respective interconnection, only a single unitary subassembly 110, as shown in FIGS. 6 and 7, has to be inserted into the housing 20. The unitary subassembly 110 will only fit into the interior of the housing 20 if the guiding ribs 78 are properly aligned with and inserted into the grooves 115 in the housing 20. Further, the unitary subassembly 110 will stop moving distally into the housing 20 during manufacturing when the distal end of the top most guiding rib 78 (if there is more than one, such as shown in FIG. 2B), reaches the distal end of groove 115, further helping ensuring proper positioning and alignment of the unitary subassembly 110 within the housing 20. Additionally, opening 70a on the front of the battery chassis/stroke limiter 70, seen in FIG. 2B, provides access to the drive mechanism 50, which is contained therein. During assembly of the unitary subassembly 110, once the drive mechanism 50 has been inserted into the battery chassis/stroke limiter 70, access to the drive mechanism 50 can still be had to perform actions such as potting, or soldering of wiring between the drive mechanism 50 and the control circuit board 100. All of these features and aspects help to simplify and streamline manufacturing. The battery chassis/stroke limiter 70 is made of a unitary piece of durable and resilient material, such as plastic, ABS (acrylonitrile butadiene styrene), or the like, that can be molded.

FIG. 3A is a front view of a housing interlock 90 according to one embodiment of the invention. Housing interlock 90 includes body 91, which in this embodiment is a generally hollow cylindrical shape. For illustrative purposes, body 91 has a central axis generally aligned with the longitudinal axis of housing 20. The housing interlock 90 includes a receptacle 92 for holding a catalyst pellet 150. The catalyst pellet 150 is used for neutralizing any outgassing of the battery 80.

The housing interlock 90 includes slots 93, through the front and rear surfaces thereof, as shown in FIGS. 3A and 3B. During manufacture, when the interlock housing 90 is attached to the battery chassis/stroke limiter 70, tabs 73 on the battery chassis/stroke limiter snap into the slots 93, and help properly position and align the two components 70, 90 with respect to each other, as well as the battery 80 held within the two components. The housing interlock 90 includes grooves 94 on the front and rear surfaces thereof, as shown in FIGS. 3A and 3B. The grooves 94 are designed to interface with ribs 74 on the front and rear of the battery chassis/stroke limiter 70. During manufacture, when the interlock housing 90 is attached to the battery chassis/stroke limiter 70, the ribs 74 on the battery chassis/stroke limiter slide into the grooves 94 on the housing interlock 90, and help properly position and align the two components 70, 90, with respect to each other, as well as the battery 80 held within the two components. The housing interlock 90 also has angle support brackets 96 located on the front of thereof. The angle support brackets 96 are used to hold the control circuit board 100 in position and prevent rattling and vibration of the control circuit board 100, which can cause failure of the control circuit board and noise and vibration that can be transmitted to the hand of the operator, causing a less satisfactory user experience.

Housing interlock 90 further includes housing interlock tabs 95. Housing interlock tabs 95 are arranged to fixedly engage to corresponding grooves 115 shown in FIG. 8, on an interior surface of the housing 20 proximal end, as well as slots in the end cap tabs 125 on the end cap 120. Alternatively but not shown, the slots and tabs on each element could be exchanged, staying within the scope of the invention. Housing interlock 90 is arranged to reside in resilient contact with the proximal end of the housing 20 by means of compression pressure between the housing interlock tabs 95 and grooves 115.

FIG. 3B provides a rear view of the housing interlock 90. In addition to the slots 93 and groove 94 previously discussed, the rear of the housing also comprises a U-support 97 near the proximal end of the housing interlock. The U-support 97 is of a size and shape such that when the unitary subassembly 110 is inserted into housing 20, the U-support makes contact with the inside rear face of housing 20 to provide support for the unitary subassembly 110 and limit movement of the unitary subassembly within the housing. At least one rib 98 on each side of the housing interlock 90 will engage in corresponding grooves 115, shown in FIG. 8, that run along both sides of the inside of housing 20 to prevent the housing interlock 90 and battery 80 from rotating within the housing 20. The rib 98 also serves to protect components during sudden axial motion by absorbing force as well as limiting rotation. Further, the rib 98 serves to simplify factory manufacturing process, as described in more detail in association with FIGS. 6 and 7, below.

A coil winding surface is disposed at the proximal end of housing interlock 90, which is arranged to receive a coil winding of conductive wire 140 sufficient to permit inductive charging of rechargeable battery 80. The particular coil winding surface can vary in size in order to accept different wire diameters and types. Not shown is that the coil winding 140 is disposed in electrical communication with the battery 80 via control circuit 100 which in this case performs a function of a charging control circuit. Housing interlock 90 helps hold the various components of the unitary subassembly 110 together during manufacturing and greatly simplifies the insertion of the unitary subassembly 110 into housing 20 in proper alignment prior to the end cap 120 being inserted. Housing interlock 90 provides structural integrity in a flexible arrangement, and is constructed of a unitary piece of durable and resilient material, such as plastic, ABS (acrylonitrile butadiene styrene), or the like, that can be molded.

Figure 4:
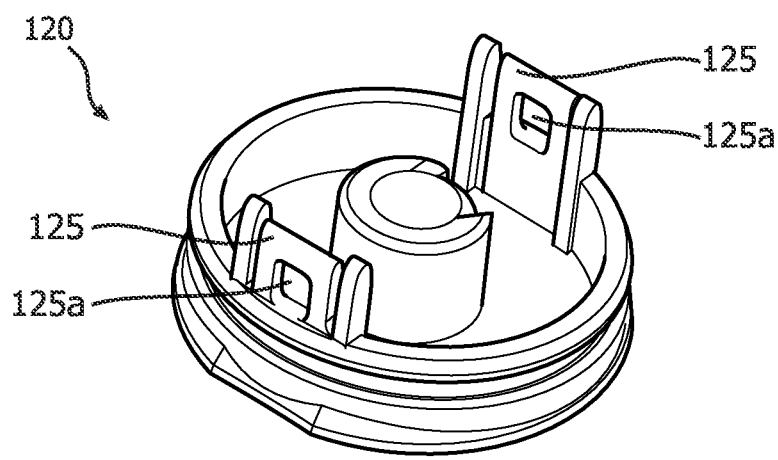
FIG. 4 is an end cap portion of a housing interlock for a power toothbrush of the present invention.

FIG. 4 shows an end cap 120 according to an embodiment of the present invention. The end cap 120 has end cap tabs 125 designed to interface with the housing interlock tabs 95 of the housing interlock 90 and the proximal end of the grooves 115 of frame 20, shown in FIG. 8. Each end cap tab 125 has a slot 125a therein.

FIG. 5A illustrates a cut-away view of the housing interlock 90. The shape and angles of the housing interlock tabs 95 can be seen clearly. When the various components comprising the unitary subassembly have been partially assembled, the housing interlock is affixed at the proximal end of the battery 80, to form the unitary subassembly 110, as seen in FIG. 7, and the unitary subassembly 110 is inserted into housing 20. Housing interlock tabs 95, slide into the grooves 115 at the proximal end of each side of the housing 20, as seen in FIG. 8. Each housing interlock tab 95 has a finger, 95a at the proximal end that is shaped and configured to interface with the slots 125a, on the end cap 120.

Once the unitary subassembly 110 is slid into the opening at the proximal end of the housing, the housing interlock tabs 95 of the housing interlock 90, when fully inserted into the grooves 115 on the interior of the housing 20, will flare outwardly toward the housing to secure the assembly in place within the housing. The weight of the battery 80 will press down on the housing interlock 90, which will cause the housing interlock tabs 95 to press outwardly slightly in the proximal end of the grooves 115 in the interior of the housing 20.

Once the unitary subassembly 110 is fully inserted in housing 20, the end cap 120, along with gasket 130 is inserted into the opening in the proximal end of the housing 20 as seen in FIG. 5B. The gasket 130 provides protection against water incursion into the interior of the housing, and ensures a snug seal of the end cap 120 into the base of the housing 20, which serves to secure the various components in place. In FIG. 5B the fingers 95a are not visible, because they are inserted in the slots 125a of end cap 120, forming a secure interlock of the end cap 120 with the housing interlock 90. This induces a reaction force on housing interlocktabs 95 in the proximal and outward directions, i.e. toward the grooves 115 on the interior surface of the housing 20. Such a result is beneficial because in the event of axial shock in the device, the housing interlock tabs 95 will be pressed more forcefully into the housing.

FIG. 5C illustrates another view of the housing interlock 90, in which the end cap 120 is fully inserted into the opening in the proximal end of the housing 20 It can be seen that housing interlock tabs 95 are aligned with the grooves 115 on the interior of the housing 20, and are held in place by means of the tab fingers 95a being interlocked with the slots 125a on the end cap tabs 125. As can be seen, when all the parts are properly inserted and positioned, the proximal end of end cap 120 is flush with the proximal end of housing 20 and seals the interior of the housing from ingress of water and other contaminants.

FIG. 6 shows an exploded view of the components of a power toothbrush 10 of the present invention. The drive shaft 60, which can be seen in FIG. 1, drive mechanism 50, battery chassis stroke limiter 70, control circuit board 100, battery 80, housing interlock 90 and various other components are assembled together to form the unitary subassembly 110, which is seen in assembled form in FIG. 7. The unitary subassembly 110 is then inserted into the proximal end of the housing 20 as a single unit, and the unitary subassembly 110 is properly aligned and resiliently held in contact with the housing 20 by means of housing interlock tabs 95 on the housing interlock 90 sliding into the corresponding grooves 115 in the interior of the housing 20. The grooves 115 are seen clearly in FIG. 8. Once the unitary subassembly 110 is fully inserted in the housing, the gasket 130 and end cap 120 are inserted into the opening at the proximal end of the housing 20. Insertion is complete when the finger 95a on housing interlock tabs 95 snap into the slots 125a on the end cap tabs 125. This applies outward pressure on the housing interlock tabs 95 against the slots on the interior of the housing 20, securing the various components in the housing, and upward pressure is applied by the end cap 120. It can be seen that the resilient contact also provides mitigation for tolerance errors in the assembly.

FIG. 7 shows an assembled view of the unitary subassembly 110. The various components are held together primarily through the interlocking relationship of the battery chassis/stroke limiter 70 and the housing interlock 90. Because all of the subcomponents are held together in the single unitary subassembly 110, it can be easily slid into the opening in the proximal end of the housing 20 for final assembly of the power toothbrush 10

FIG. 8 is a view of the interior of the housing 20 from the opening at the proximal end thereof. The groove 115, which extends approximately one half way up one side of the interior wall of the housing 20 can be seen. The guiding ribs 78 of the battery chassis/stroke limiter 70 are designed to fit into groove 115 at the distal end thereof, aligning with the upper limit of the groove 115. Ribs 98 of housing interlock 90 also fit into the grooves 115 to maintain alignment of the unitary subassembly 110 in the housing 20. As can be seen in FIG. 8, the proximal end of groove 115 is flared out, and of a shape and size to accommodate end cap tabs 125 of end cap 120 which are connected to the housing interlock tabs 95 of housing interlock 90 by means of interlock housing tab fingers 95a. The gasket 130 of end cap 120 fits up against the ridge that runs around the circumference of the interior of the housing 20 to form a tight seal against the egress of fluids.

The contemplated scope of the inventions that are described here pertain to various modifications as well. Minor changes to the geometry of the battery chassis stroke limiter 70 and housing interlock 90 in particular fall within the claimed scope, as long as the geometry fulfills the described functions and advantages.

What is claimed is:

1. A battery chassis/stroke limiter for a power toothbrush having a housing, comprising:
    a substantially hollow interior for holding a portion of a rechargeable battery that powers the power toothbrush;
    tolerance compensation leaves disposed in a compressive arrangement between a distal end of the battery and the distal portion of the battery chassis/stroke limiter;
    first, second and third battery hardstops; and
    guiding ribs for compressibly holding the battery chassis/stroke limiter in grooves on the interior of the housing.

2. The battery chassis/stroke limiter of claim 1 wherein the tolerance compensation leaves are arranged to absorb energy from motion of the battery.

3. The battery chassis/stroke limiter of claim 2 wherein the tolerance compensation leaves are further arranged to slow sudden acceleration of the battery.

4. The battery chassis/stroke limiter of claim 1 wherein the first, second and third battery hardstops includes at least one compression surface, disposed at the proximal end of the hard stop, closest to the battery, which is shaped such that if it contacts a portion of the distal end of the battery, battery motion is limited and absorbed.

5. The battery chassis/stroke limiter of claim 1 further comprising horizontal stops on a front and rear of the battery chassis/stroke limiter to limit distal direction movement of the battery and stop displacement.

6. The battery chassis/stroke limiter of claim 1 further comprising battery chassis tabs and ribs to interface with a component of the power toothbrush that holds another portion of the battery.

7. The battery chassis/stroke limiter of claim 1 wherein the guiding ribs absorb vibration from the battery during operation to reduce vibration transmitted to the housing.

8. The battery chassis/stroke limiter of claim 1, wherein the battery chassis/stroke limiter is made of a unitary piece of durable and resilient material, such as plastic, ABS (acrylonitrile butadiene styrene) that can be molded.

9. A system for mitigating mechanical shock in a power toothbrush, comprising:
- an elongated housing open at a distal end and a proximal end;
- a unitary subassembly disposed within the housing having;
- a drive mechanism having a drive shaft at a distal end thereof, the drive shaft projecting through the opening at the distal end of the elongated housing, the drive shaft configured to receive a toothbrush brushhead,
- a battery
- a control circuit in electrical communication with the battery;
- a battery chassis/stroke limiter for holding at least a portion of the battery, the battery chassis/stroke limiter including tolerance compensation leaves, and first, second and third battery hardstops;
- a housing interlock for holding at least a portion of the battery disposed in resilient contact with grooves in the interior wall of the proximal end of the housing configured to hold together in compressive pressure the components of the unitary subassembly;
- and an end cap having end cap tabs wherein the housing interlock and the end cap are fixedly engaged together by means of a slot on end cap tabs and a finger on corresponding housing interlock tabs disposed on the housing interlock, the housing interlock tabs and end cap tabs disposed in resilient contact with the grooves in the elongated housing to resiliently secure the unitary subassembly in the housing.

10. The system of claim 9, wherein the tolerance compensation leaves contact a distal end of the battery during normal operation of the power toothbrush to mitigate mechanical shock.

11. The system of claim 9, wherein the first, second and third battery hardstops contact a distal end of the battery if the power toothbrush experiences unexpected axial or distal motion to prevent damage to the battery or other components of the unitary subassembly in the housing.

12. The system of claim 9 wherein the housing interlock tabs are arranged to displace toward the interior surface of the housing in response to a flexure of the end cap tabs.

13. The system of claim 9 wherein the housing interlock is sized to absorb axial shock originating if the toothbrush is dropped.

14. The system of claim 9 wherein the housing interlock further comprises a U-support near a proximal end thereof to limit movement of the unitary subassembly within the housing to mitigate mechanical shock.

15. The system of claim 9 wherein tolerance compensation leaves, and battery hardstops provide for drop mitigation protection and shock protection if the power toothbrush is dropped.

* * * * *